United States Patent [19]

Riedlinger

[11] Patent Number: 5,209,221
[45] Date of Patent: May 11, 1993

[54] ULTRASONIC TREATMENT OF PATHOLOGICAL TISSUE

[75] Inventor: Rainer Riedlinger, Karlsruhe, Fed. Rep. of Germany

[73] Assignee: Richard Wolf GmbH, Knittlingen, Fed. Rep. of Germany

[21] Appl. No.: 763,475

[22] Filed: Sep. 20, 1991

Related U.S. Application Data

[63] Continuation of Ser. No. 315,448, Feb. 24, 1989, abandoned.

[30] Foreign Application Priority Data

Mar. 1, 1988 [DE] Fed. Rep. of Germany ....... 3806532

[51] Int. Cl.$^5$ ............................................ A61H 23/00
[52] U.S. Cl. ............................. 128/24 AA; 128/24 EL
[58] Field of Search ........ 128/24 EL, 660.03, 24 AA; 606/127, 128; 310/317, 335

[56] References Cited

U.S. PATENT DOCUMENTS

| | | | |
|---|---|---|---|
| 3,237,623 | 3/1966 | Gordon | 128/24 AA |
| 3,499,437 | 3/1970 | Balamuth | 128/24 A |
| 3,526,219 | 9/1970 | Balamuth . | |
| 3,589,363 | 6/1971 | Banko . | |
| 3,735,755 | 5/1973 | Eggleton et al. | 128/24 AA |
| 3,941,122 | 3/1976 | Jones | 128/24 A |
| 4,315,514 | 2/1982 | Drewes et al. | 128/653 |
| 4,618,796 | 10/1986 | Riedlinger | 310/311 |
| 4,622,972 | 11/1986 | Giebeler, Jr. . | |
| 4,664,111 | 5/1987 | Reichenberger | 128/24 A |
| 4,671,254 | 6/1987 | Fair | 128/24 A |
| 4,674,505 | 6/1987 | Pauli et al. | 128/24 EL |
| 4,696,425 | 9/1987 | Landes | 228/1.1 |
| 4,721,106 | 1/1988 | Kurtze et al. . | |
| 4,819,621 | 4/1989 | Ueberle et al. | 128/24 |
| 4,827,911 | 5/1989 | Broadwin et al. | 128/24 A |
| 4,858,597 | 8/1989 | Kurtze et al. | 128/24 A |
| 5,054,470 | 10/1991 | Fry et al. | 128/24 AA |

FOREIGN PATENT DOCUMENTS

| | | |
|---|---|---|
| 3300121 | 7/1983 | Fed. Rep. of Germany . |
| 3331510 | 3/1984 | Fed. Rep. of Germany . |
| 3527586 | 12/1986 | Fed. Rep. of Germany . |
| 2113099 | 8/1983 | United Kingdom . |
| 2176110 | 12/1986 | United Kingdom . |

OTHER PUBLICATIONS

F. J. Fry, "Precision High Intensity Focusing Ultrasonic Machines for Surgery," *Am. J. Physical Med.*, vol. 37, No. 3, p. 152 (Jun. 1958).

L. D. Rosenberg, "La Generation et l'Etude des Vibrations Ultra-Sonores de Tres Grande Intensite," *Acustica*, vol. 12, p. 40 (1962).

P. P. Lele, "Production of Deep Focal Lesions by Focused Ultrasound—Current Status," *Ultrasonics*, Apr. 1967, p. 105.

L. R. Gavrilov, N. P. Narbut and F. E. Fridman, "Use of focused ultrasound to accelerate the 'maturing' of a cataract," *Sov. Phys. Acoust.*, vol. 20, No. 3, p. 229 (Nov.-Dec. 1974).

D. J. Coleman, F. L. Lizzi, and F. A. Jakobiec, "Therapeutic Ultrasound in the Production of Ocular Lesions," *Am. J. Ophth.*, 86:185, 1978.

(List continued on next page.)

Primary Examiner—Lee S. Cohen
Assistant Examiner—Kevin Pontius
Attorney, Agent, or Firm—Panitch Schwarze Jacobs & Nadel

[57] ABSTRACT

A device for generating sonic signal forms for limiting, preventing or regressing the growth of pathological tissue comprises an ultrasonic transmission system for transmitting sound waves, focussed on the tissue to be treated, by way of a coupling medium. An ultrasonic signal produced at the focus of the system comprises brief pulses having at least one rarefaction phase with a negative sonic pressure amplitude with a value greater than $2 \times 10^5$ Pa. The ultrasonic signal is radiated with a carrier frequency exceeding 20 kHz, a sonic pulse duration T of less than 100 µs and a pulse recurrence rate of less than 1/(5T). The device produces controlled cavitation in the tissue to be treated.

30 Claims, 4 Drawing Sheets

OTHER PUBLICATIONS

D. J. Coleman, F. L. Lizzi, A. A. M. El-Mofty, J. Driller, and L. A. Franzen, "Ultrasonically Accelerated Resorption of Vitreous Membranes," *Am. J. Ophth.*, 89:490 1980.

D. J. Coleman, F. L. Lizzi, S. Chang, and J. Driller, "Applications of Therapeutic Ultrasound in Ophthalmology," *Prog. in Med. Ultrasound*, vol. 2, 1981, p. 263.

F. L. Lizzi, J. Driller, and M. Ostromogilsky, "Thermal Model for Ultrasonic Treatment of Glaucoma," *Ultrasound in Med. & Biol.*, vol. 10, No. 3, p. 289 (1984).

Brendel et al., "Effect of Shock Waves on the Microvasculature", Prog. Appl. Microcirc., vol. 12, pp. 41–50 (1987).

Wilmer et al., "Effeckt von Stosswellen auf Tomorzellen in Suspension," 64th Convention, Union of Baravian Surgeons (Jul. 1987).

Eugen Skudrzyk, *The Foundations of Acoustics*, pp. 295–296, Springer-Verlag, Wien–New York (1971).

Heinrich Kuttruff, *Room Acoustics*, p. 22, Applied Science Publishers Ltd., London (1973).

ULTRASONIC TREATMENT OF PATHOLOGICAL TISSUE

CROSS-REFERENCE TO RELATED APPLICATION

This is a continuation of copending application Ser. No. 315,448, filed Feb. 24, 1989, now abandoned.

FIELD OF THE INVENTION

This invention relates to a device for producing ultrasonic signal forms for limiting, preventing or regressing the growth of pathological tissue, that is to say, for the medical treatment of such tissue, by means of an ultrasonic transmitter system.

BACKGROUND OF THE INVENTION

Surgical instruments and surgical methods, as well as methods of chemotherapy, and methods of, and instruments for, radiation therapy and hyperthermic treatment are known for the medical treatment of proliferating tissue, although methods of acoustic surgery for that purpose have not presently been widely accepted in clinical practice.

For acoustic surgery, a mechanically oscillated hollow metal pin, for example, is used as a therapeutic tool. Such an instrument is described for example, in DE-A-35 27 586, and analogous devices for the removal of tissue by ultrasonic surgery are disclosed in U.S. Pat. No. 3,526,219 and U.S. Pat. No. 3,589,363. The attainments of such mechano-acoustic methods, however, extend from the reversible scrambling of the cell contents to the disintegration to a great extent of membranes, mitochondria and cell nuclei.

Ultrasonic instruments and methods acting hyperthermically are known, for example, from DE-A-33 31 510, DE-A-33 00 121 and DE-A31 50 513. Nevertheless, these non-surgical instruments and methods, for the treatment of tissues, in particular proliferating tissues, in human beings and animals must presently be regarded as experimental. This is also the case in respect of the non-surgical acoustic systems which do not operate hyperthermically, for the treatment of proliferating tissues in human bodies. Treatment by means of a hyperthermically operating device is based upon the appreciation that tumors are killed at a temperature of say 42.5° C. when maintained for a protracted period. Raising the temperature locally within the body presents difficulties, however, since the tissue is cooled by the perfusion of blood and comparatively protracted high sonic intensities are needed to bring about a substantial temperature rise. These high sonic intensities may, however, cause cavitations in, and consequential injury to, healthy tissue in front of the tumor.

But little information has been published in the field relating to methods of treating proliferating tissues, which are non-surgical and acoustic and do not act hyperthermically.

DE-A-35 44 344, for example, discloses a device for inhibiting the growth of new pathological forms in living organisms, in which blood vessels are thrombosed by means of focussed shock waves, a once-only positive pressure pulse being generated for this purpose. The following effects of shock waves on tissues are disclosed in the publication "Prog.app.Microcirc.", vol.12, pages 41 to 50, 1987: vasoconstriction, stasis in capillaries, microhaemorrhages, the emergence of macromolecules from venules, the formation of conglomerates in venules, haemorrhages and the formation of haematoma, the destruction of vascular walls, the destruction of lining cells and the issue of red blood cells from blood vessels. This publication is silent, however, as to the treatment of tumors.

During the 64th convention of Bavarian Surgeons in July 1987 at Bad Reichenhall, Wilmer, Delius and Brendel reported on the effect of shock waves on tumorous cells in vitro, with reference to the so-called "ratio of adoption". At the same venue, Goetz, Konigsberger, Conzen and Brendel reported on the effect of shock waves on tumor microcirculation and tumor growth in the case of Syrian golden hamsters. There were reports upon the following effects: microhaemorrhages, extravasation of macromolecules, intravascular thrombosing actions and temporary arteriole constrictions. Tumor colliquations were obtained by a repetitive treatment by means of series of shock waves.

SUMMARY OF THE INVENTION

In the light of the foregoing, the present invention is intended to solve the problem of providing a device for the acoustic non-surgical and non-hyperthermically acting treatment of selected sections of tissue, and which generates ultrasonic signal forms which may well permanently inhibit, prevent or catabolise the growth of pathological tissue, but which should not injure surrounding healthy tissue either temporarily or permanently.

This problem is solved in a device for generating ultrasonic signal forms limiting, preventing or regressing the growth of pathological tissue or the like by means of an ultrasonic transmission system focussed on the tissue to be treated, which transmits sound waves under a coupling condition preferably established by way of a fluid coupling medium; in that for the purpose of generating controlled cavitation (as defined below), the device produces an ultrasonic signal at the focus of an ultrasonic transmitter system, the briefly emitted sound pulses of which have at least one rarefaction phase of negative sonic pressure amplitude exceeding $2 \times 10^5$ Pa in value, the ultrasonic signal having a carrier frequency exceeding 20 kHz, a sonic pulse duration T of less than 100 μs and a recurrence rate of less than $1/(5T)$.

The ultrasonic signal forms produced by the device, at the focus of the ultrasonic transmitter system that it controls, generate controlled cavitation with collapse of the cavitation blisters assisted by the positive pressure phase, in the tissue to be treated, as a result of localised sonic pressure concentration, without at the same time generating any temperature rise such as to have a hyperthermic effect. The sonic pulses are brief enough to contain so little acoustic energy for absorption by the tissue to be treated that practically no sonically engendered temperature rise can be detected in the living perfused tissue. In order to reduce the absorbable acoustic energy, intervals of longer duration may be provided between the sonic pulses, the duration of which intervals may amount to a multiple of the signal duration and may even exceed it by several orders of magnitude. For example, a signal duration of 20 μs and an interval of 0.5 s may be taken as typical. Such a protracted interval allows extensive or complete regeneration of gas filled cavitation blisters and thus again the generation of specific controlled cavitation after the next brief sonic action pulse.

The term "specific cavitation", as used herein, means that the instant of the onset of cavitation is precisely controllable and that the focus remains strictly circumscribed within the focal area. In contrast, the term "controlled cavitation", as used herein, means that the radius of the cavitation blisters can be adjusted precisely to small values. The device according to the invention has the advantages that it is capable of preventing considerable and uncontrolled blister growth such as is produced during protracted intensive ultrasonic impingement, as in shock wave generating systems, and that the high sonic pressure shock wave amplitudes are avoided.

By virtue of the brevity of each sonic pulse, the minute cavitation blisters produced during the negative pressure phase thereof collapse with the aid of ambient pressure and the surface tension of the blisters, and the positive pressure phases of the brief sonic signal promote the collapse of the blisters. If said minute cavitation blisters are gas-free or at least gaspoor, numerous localised and minute shock wave sources are created by their collapse the surge intensities of which are considerably greater than where blister collapse is unassisted by positive pressure phases.

The occurrence of specific and controlled cavitation, as well as the production described above of numerous minute sonic surges within the focal area, which is spatially restricted to the tissue to be treated, contribute to the solution of the problem set forth above.

Although the variety of the tissues to be treated necessitates adaptation of the sonotechnic parameters, the parametric limits thereof may be defined quantitatively as follows:

Carrier frequency f of the sonic pulse signal:

$20 \text{ kHz} < f < 10 \text{ MHz}$

Duration T of the sonic pulse signal:

$100 \text{ ns} < T < 100 \text{ } \mu s$

Amplitude p− of the negative pressure phase(s):

$2 \times 10^5 \text{ Pa} < /p-/ < 2 \times 10^8 \text{ Pa}$

Amplitude p+ of the positive pressure pahse(s):

$0 < p+ < 4 \times 10^8 \text{ pa}$

Recurrence rate r (pulse succession frequency):

$1/60 \text{ s} < r < 1/(5T)$

Also, the envelope profile of the sonic pulse signal and the initiation of the sonic signal by a positive pressure or a rarefaction phase are other parameters that must be taken into account in producing sonic pulses barely below the cavitation threshold that is to say for producing controlled tissue cavitation.

For treating a particular type of tissue, in a predetermined part of the body, the selection of the parameters should be made in the light of clinical experience, within the limits specified, with the object of exploiting the acoustically generated mechanical displacement of the components of the proliferating cell area to cause mechanically induced significant alterations in the tissue environs and/or alterations in the tissue cells themselves. Such alterations are indicated by a fall in, an obstruction of, or even an interruption of, the blood supply to a cell, as well as by acoustically induced interference with the existing mode of nutrition of the cell, and/or by destruction of the cell elements (rips in the cell membranes, destruction of elements of the cell contents), but not by destruction of the structural cohesion of the cell aggregate.

In principle, the carrier frequency, the duration of the sonic pulse signal and the amplitude and duration of the negative pressure phase, are the essential quantities which determine the cavitation threshold in a preselected tissue. The higher is the carrier frequency, the shorter are the sonic pulse and negative pressure phase durations and the lower is the amplitude of the negative pressure phase, the more unlikely will be the onset of cavitation.

A carrier frequency of between 0.2 and 4 MHz has proved to be particularly advantageous, the duration of a single negative pressure phase of the sound waves applied at the focus being consequently shorter than 2.5 $\mu s$.

The chronological course of the envelope profile of the sonic pulse, at the focus, may represent an exponential function, a Gaussian function, a stepwise function, or a rectangular wave function, for example.

The envelope profile of the sonic pulse signals controls the chronological course of the growth of blisters caused by equidirectional diffusion, and those envelope profiles specified above have been found to be particularly advantageous, the appropriate envelope profile being selected in accordance with the treatment that is needed.

The ultrasonic transmitter system may be a focussing piezoelectric mosaic or matrix emitter comprising a partially absorbent backing, such as a magnetic sonic burst transmitter operating in accordance with the eddy current, parallel wire or magnetostriction principle.

The transmitter may, however, also be a known sound source, operating in accordance with the steam blister explosion principle. To this end, it should be provided with two focussing reflectors, the first of which reflects in a soft manner and the second of which reflects in a or so called "hard" manner, said reflectors being so staggered spatially with respect to the sound source, that a sonic signal of alternative prefix, a positive pressure phase being followed by a negative pressure phase or vice versa, is produced in the focal area common to the first reflector and to the twin reflector constituted by the first and second reflectors.

The transmitter system may, according to another embodiment, comprise a sound source operating in accordance with the steam blister principle and being provided with two focussing and mutually confronting reflectors, the first of which reflects in a soft manner and the second of which reflects in a hard manner, the reflectors being so arranged and offset spatially with respect to said sound source that a sonic signal of alternative prefix is generated in the common focal area of the reflectors. The reflectors may also be of co-axial ellipsoidal/annular construction.

DETAILED DESCRIPTION OF THE INVENTION

Figure 1:
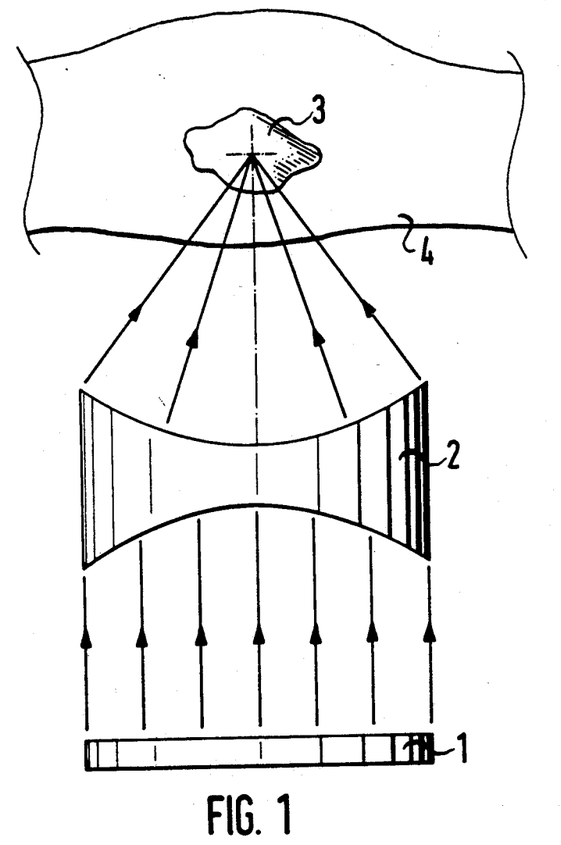
FIG. 1 is a diagram of an ultrasonic transmitter system comprising a plane sonic emitter and a focussing acoustic lens, in use in treating pathological tissue.

As shown in FIG. 1 a device according to an embodiment of the invention comprises an ultrasonic transmitter system 1,2 which produces ultrasonic signals in a focal area 3. The transmitter system comprises a plane sound emitter 1, of which the emitted beam is focussed by means of an acoustic lens 2 into pathological tissue 4 in a human body, to be treated.

The transmitter system may for example be constructed as a focussing piezoelectric matrix transmitter having a partially absorbent backing, as a magnetic sonic burst transmitter operating in accordance with the eddy current, parallel wire or magnetostriction principle.

Examples of the ultrasonic signals produced in the focal area 3 for the purpose of limiting, preventing or regressing the growth of the tissue to be treated, are shown in FIGS. 2 to 6.

Figure 2:
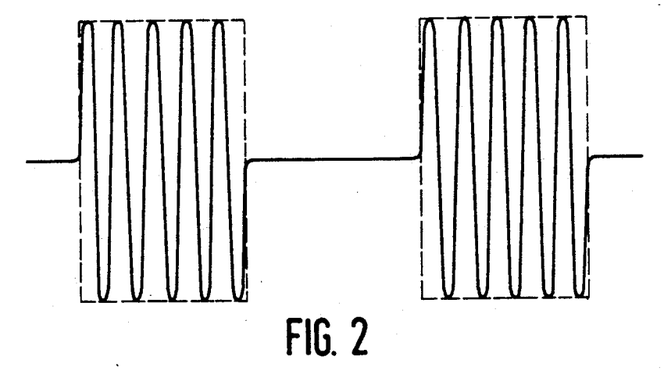
FIGS. 2 to 6 are graphs illustrating sonic pulse trains having different envelope profiles.
Figure 3:
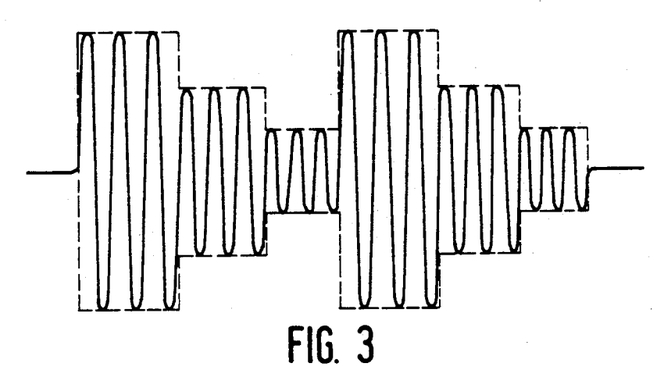

It is unimportant whether controlled cavitation produced in the tissue is produced by means of a cyclic rectangular envelope profile sonic pulse train according to FIG. 2 or by means of a pulse train having a stepped or stair-shaped profile envelope as shown in FIG. 3. Since, however, the primarily formed radii of the cavitation blisters and their growth are determined by the envelope profile amplitude and its chronological course, an envelope profile should be selected, which is adapted to the treatment that is needed, as stated above.

Figure 4:
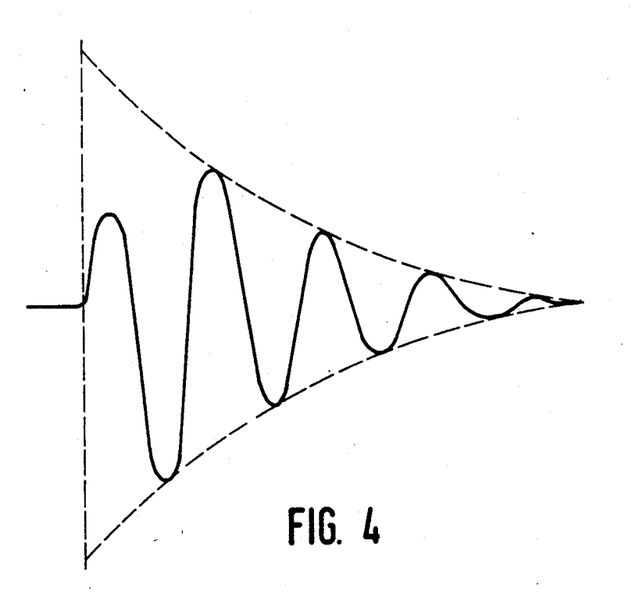
Figure 5:
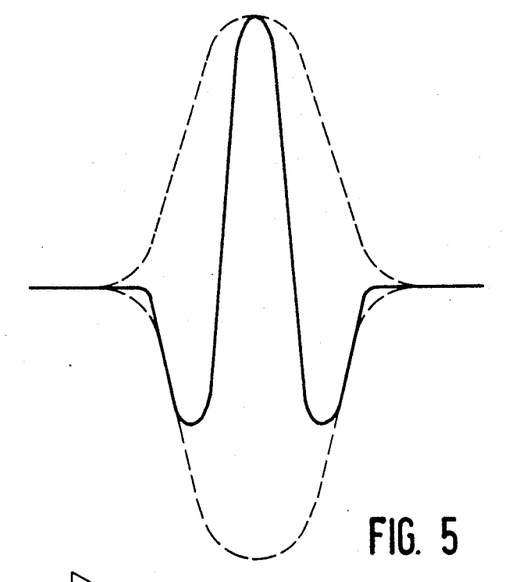
Figure 6:
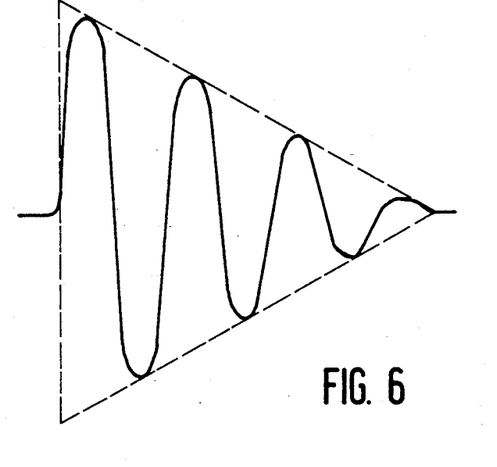

An envelope profile representing a decaying exponential function according to FIG. 4 proved to be advantageous, as well as an envelope profile representing a Gaussian function, as shown in FIG. 5, or linear slope function as shown in FIG. 6.

Given the same carrier frequency and identical peak amplitudes and durations of the envelope profiles, a sonic pulse train having a rectangular envelope profile generates the greatest amount of blister growth.

Figure 7:
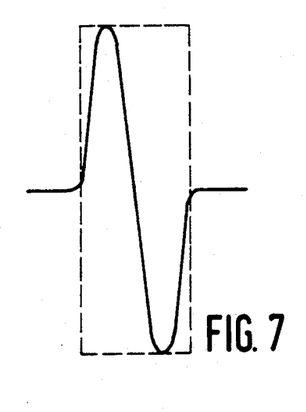
FIG. 7 is a graph illustrating a sonic pulse train having an envelope of rectangular profile and starting with a positive pressure phase.
Figure 8:
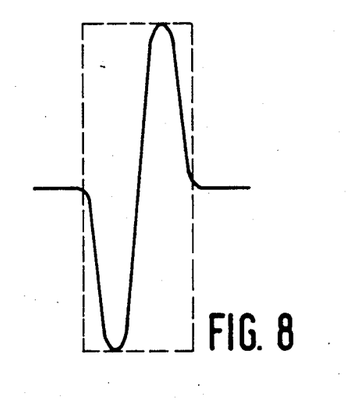
FIG. 8 is a graph illustrating a sonic pulse train having an envelope of rectangular profile and starting with a negative pressure phase.

Importantly, however, the rectangular envelope profile according to FIG. 2, allows of generating a sonic pulse having a single oscillation period, as shown in FIGS. 7 and 8, it being particularly advantageous if the concomitantly bipolar sonic signal starts with the rarefaction phase as shown in FIG. 8. A single cavitation blister collapse assisted by sonic pressure may thereby be obtained by appropriate selection of the cycle duration and of the rarefaction amplitude, such collapse generating localised secondary shock waves, the shock or surge amplitudes of which considerably exceed the surge amplitudes caused by normally collapsing cavitation blisters if these collapse only as a result of ambient pressure and of blister surface tension, that is to say without the assistance of the positive pressure phase.

If the duration of the pulse measured at the focus, is identical with the cycle length of the carrier frequency and is synchronised with its passages through zero, the growth of cavitation blisters can be prevented by equidirectional diffusion. The intervals between the sonic pulses should, however, be longer by approximately one order of magnitude than the sonic pulse duration.

A rising pulse recurrence rate increases the probability of new cavitation blisters appearing and the blister radius is increased by the action of equidirectional diffusion, which finally results in tearing of the cell membrane and thus in the destruction of the pathological tissue. If the aim is to produce sonic impingment acting directly on the cell elements, resulting in mechanical cell damage, a high pulse recurrence rate should be selected. By contrast, low pulse recurrence rates are more advantageous for causing the required interference with the nutritional condition of the cells of the pathological tissue which is to be treated, because the tissue portion acted upon sonically, is isolated from the blood supply by establishing a tissue area inhibiting the flow of blood.

Ultrasonic transmitter focussing systems will now be described with reference to FIGS. 9 to 12, which are especially adapted for use with a sonic explosion source operating on the steam bubble explosion principle as an ultrasonic transmitter.

Figures 9, 10, 11, 12:
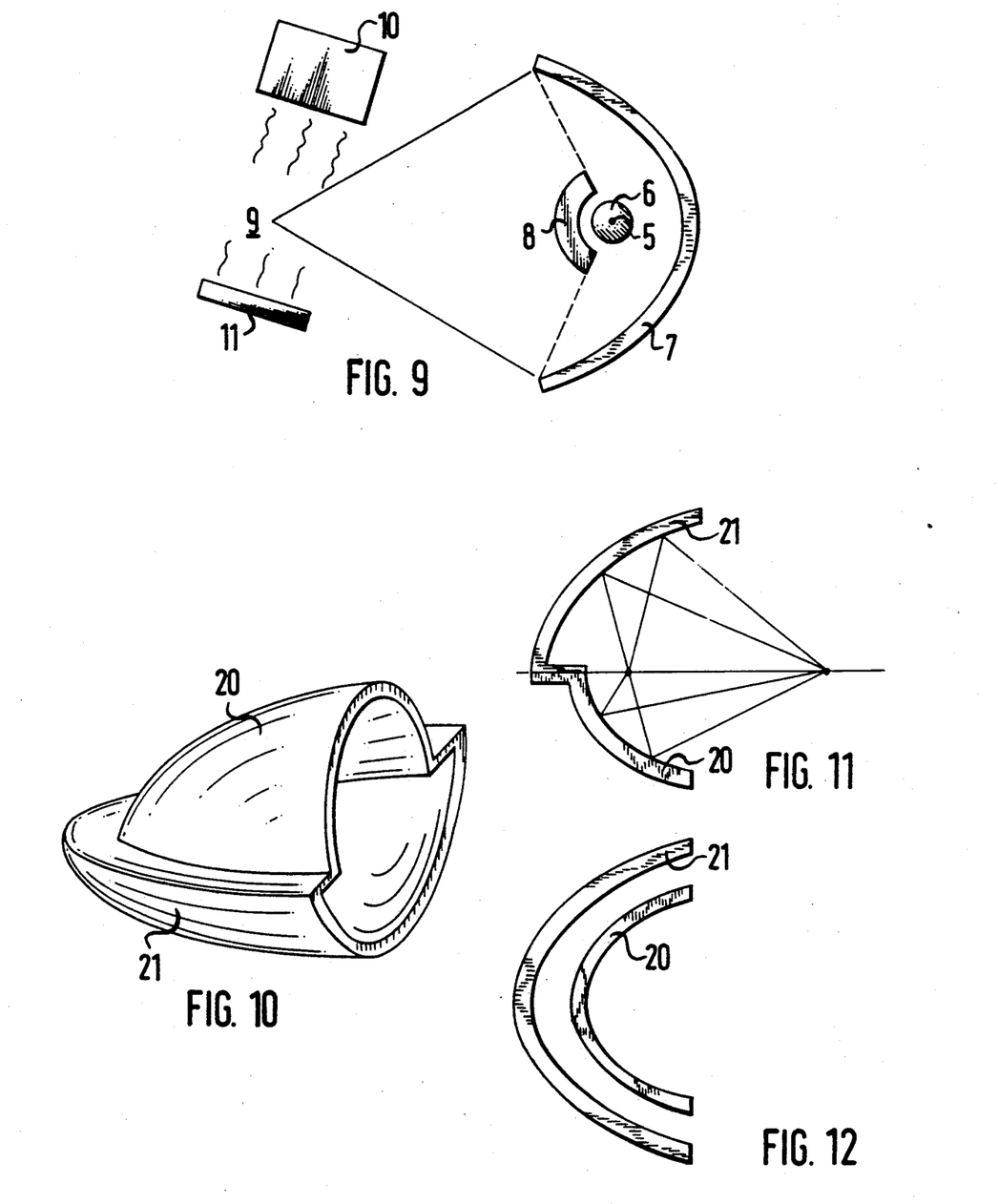
FIG. 9 is a diagram of an ultrasonic transmitter system, comprising a sonic explosion source and a two-reflector focussing system.
FIG. 10 is a diagramatic isometric view of a twin reflector focussing system for use in combination with a sonic explosion source.
FIG. 11 is a vertical sectional view through the twin reflector system of FIG. 10.
FIG. 12 is a horizontal sectional view through the twin reflector system of FIGS. 10 and 11.

As shown in FIG. 9, a first sector of a shock wave 6 generated by a sonic explosion source 5 operating according to the steambubble explosion, principle is reflected by an ellipsoidal reflector 7, a second sector of the shock wave 6 being initially reflected by a hollow spherical cap reflector 8 (one of said reflectors reflecting in a soft manner, and the other reflecting in a hard manner) and then by the reflector 7, so that a positive pressure phase is followed by a rarifaction phase or vice versa, in the focal area 9 which is common to the first reflector 7 and the twin reflector constituted by the two reflectors 7 and 8.

Advantageously, the reflector 8 covers only the sector which is not covered by the reflector 7, as shown in FIG. 9. In this case unfocussed sonic beam propagation into the body is eliminated and substantially the whole of the shock wave generated by the sonic explosion source is beamed into the focus 9.

If the reflector 8 is hard and the reflector 7 is soft, a twin pulse of which each pulse starts with a rarefaction phase is generated in the focal area 9.

The sectors covered may be determined by selecting the reflector geometries, thereby appropriately to adjust the amplitudes of the positive pressure and rarification phases of the sonic burst generated in the focal area 9.

Another form of focussing system for use with a sonic explosion source will now be described with reference to FIGS. 10 to 12, which system comprises two partial ellipsoid reflectors 20 and 21 of which the focal areas may be coincident but which cause different sonic trajectory periods between said source which is situated at the first focus and the tissue to be treated which is situated at the second focus, one reflector reflecting in a hard manner and the other in an soft manner.

This focusing system eliminates the problem of the possible onset of cavitation at the focus 9, which is encountered with the focussing system of FIG. 9, and which arises in particular, when the reflector 8 is soft, as compared with the reflector 7.

Apart from the brief sonic pulse producing means described above, there is preferably provided, a location system which allows proliferating tissue to be detected in the human body in a known manner by means of ultrasonic A or B scanning or by methods of ultrasonic mapping. To this end, the sonic therapy transmitting system may be associated with an ultrasonic A scanner, or may even be integrated therewith. The A scanning facility then allows of detecting the controlled cavitation and the shrinkage of cavitation fogging in the tissue recordable immediately after a sonic strike.

The location system may be a known X-ray system, MR system or PET system.

There is shown, by way of example in FIG. 9, a location system comprising a location transmitter 10 and a location receiver 11, for observation of the focal and treatment area 9.

A positioning system allows the proliferating tissue which is to be treated, to be placed in the focal area. Either the transmitter system, or the patient, may be moved to this end by means of a displacement system movable in the three spatial directions. The displacement system may be movable in a translatory and/or in a rotational manner.

What is claimed is:

1. An ultrasonic transmission system for the treatment of pathological tissue by producing controlled cavitation in the pathological tissue comprising:
   an ultrasonic pulse generating means comprising:
   means for generating an ultrasonic signal having a carrier frequency exceeding 20 kHz;
   means for generating pulses for controlled pathological tissue cavitation, said pulse generating means coupled to said signal generating means to generate briefly emitted pulses of said ultrasonic signal, each pulse having at least one rarefaction phase of negative sonic pressure amplitude exceeding $2 \times 10^5$ Pa in value, a pulse duration (T) of less than 100 μs, and a pulse recurrence rate of less than 1/(5T); and
   means for focussing said ultrasonic pulses, said focussing means positioned with respect to said ultrasonic pulse generating means to focus the ultrasonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
   said pulse generating means being capable of producing at said focal point a pulse envelope amplitude profile which is shaped as an exponential function.

2. An ultrasonic transmission system for the treatment of pathological tissue by producing controlled cavitation in the pathological tissue comprising:
   an ultrasonic pulse generating means comprising:
   means for generating an ultrasonic signal having a carrier frequency exceeding 20 kHz;
   means for generating pulses for controlled pathological tissue cavitation, said pulse generating means coupled to said signal generating means to generate briefly emitted pulses of said ultrasonic signal, each pulse having at least one rarefaction phase of negative sonic pressure amplitude exceeding $2 \times 10^5$ Pa in value, a pulse duration (T) of less than 100 μs, and a pulse recurrence rate of less than 1/(5T); and
   means for focussing said ultrasonic pulses, said focussing means positioned with respect to said ultrasonic pulse generating means to focus the ultrasonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
   said pulse generating means being capable of producing at said focal point a pulse envelope amplitude profile which is shaped as a Gaussian function.

3. An ultrasonic transmission system for the treatment of pathological tissue by producing controlled cavitation in the pathological tissue comprising:
   an ultrasonic pulse generating means comprising:
   means for generating an ultrasonic signal having a carrier frequency exceeding 20 kHz;
   means for generating pulses for controlled pathological tissue cavitation, said pulse generating means coupled to said signal generating means to generate briefly emitted pulses of said ultrasonic signal, each pulse having at least one rarefaction phase of negative sonic pressure amplitude exceeding $2 \times 10^5$ Pa in value, a pulse duration (T) of less than 100 μs, and a pulse recurrence rate of less than 1/(5T); and
   means for focussing said ultrasonic pulses, said focussing means positioned with respect to said ultrasonic pulse generating means to focus the ultrasonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
   said pulse generating means being capable of producing at said focal point a pulse envelope amplitude profile which is a stepped profile.

4. An ultrasonic transmission system for the treatment of pathological tissue by producing controlled cavitation in the pathological tissue comprising:
   an ultrasonic pulse generating means comprising:
   means for generating an ultrasonic signal having a carrier frequency exceeding 20 kHz;
   means for generating pulses for controlled pathological tissue cavitation, said pulse generating means coupled to said signal generating means to generate briefly emitted pulses of said ultrasonic signal, each pulse having at least one rarefaction phase of negative sonic pressure amplitude exceeding $2 \times 10^5$ Pa in value, a pulse duration (T) of less than 100 μs, and a pulse recurrence rate of less than 1/(5T); and
   means for focussing said ultrasonic pulses, said focussing means positioned with respect to said ultrasonic pulse generating means to focus the ultrosonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
   said pulse generating means being capable of producing at said focal point a pulse envelope amplitude profile which is shaped as a sloping linear function.

5. An ultrasonic transmission system for the treatment of pathological tissue by producing controlled cavitation in the pathological tissue comprising:
   an ultrasonic pulse generating means comprising:
   means for generating an ultrasonic signal having a carrier frequency exceeding 20 kHz;
   means for generating pulses for controlled pathological tissue cavitation, said pulse generating means coupled to said signal generating means to generate briefly emitted pulses of said ultrasonic signal, each pulse having at least one rarefaction phase of negative sonic pressure amplitude exceeding $2 \times 10^5$ Pa in value, a pulse duration (T) of less than 100 $\mu$s, and a pulse recurrence rate of less than 1/(5T); and
   means for focussing said ultrasonic pulses, said focussing means positioned with respect to said ultrasonic pulse generating means to focus the ultrasonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
   said pulse generating means being capable of producing at said focal point a pulse envelope amplitude profile which is a rectangular profile.

6. The ultrasonic transmission system as claimed in claim 5, wherein said pulse generating means is further characterized as capable of producing initially a rarefaction phase.

7. The ultrasonic transmission system as claimed in claim 6, wherein said ultrasonic signal generating means is further characterized as capable of producing a signal having a carrier frequency between 0.2 and 4 MHz, whereby the duration of each said rarefaction phase can be less than 2.5 $\mu$s.

8. The ultrasonic transmission system as claimed in claim 5, wherein said pulse generating means is further characterized as capable of producing pulses the duration of which measured at the focal point of said focussing means is equal to the cycle length of the carrier frequency and is synchronized with its passages through zero.

9. The ultrasonic transmission system as claimed in claim 5, wherein said ultrasonic signal generating means is further characterized as capable of producing a signal having a carrier frequency between 0.2 and 4 MHz, whereby the duration of each said rarefaction phase can be less than 2.5 $\mu$s.

10. An ultrasonic transmission system for the treatment of pathological tissue by producing controlled cavitation in the pathological tissue comprising:
    an ultrasonic pulse generating means comprising:
    means for generating an ultrasonic signal having a carrier frequency exceeding 20 kHz;
    means for generating pulses for controlled pathological tissue cavitation, said pulse generating means coupled to said signal generating means to generate briefly emitted pulses of said ultrasonic signal, each pulse having at least one rarefaction phase of negative sonic pressure amplitude exceeding $2 \times 10^5$ Pa in value, a pulse duration (T) of less than 100 $\mu$s, and a pulse recurrence rate of less than 1/(5T); and
    means for focussing said ultrasonic pulses, said focussing means positioned with respect to said ultrasonic pulse generating means to focus the ultrasonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
    said pulse generating means producing at said focal point a pulse envelope amplitude profile which is adapted to the treatment that is needed, and
    said focussing means further comprising first and second focussing reflectors one of which reflects in a soft manner and the other of which reflects in a hard manner, said reflectors being so staggered spatially with respect to said signal generating means and said pulse generating means so that said signal is a signal of alternative prefix and is produced in a common focal area of the first reflector and of a combination of the second reflector with the first reflector.

11. The ultrasonic transmission system as claimed in claim 10, wherein said pulse generating means is further characterized as capable of producing initially a rarefaction phase.

12. The ultrasonic transmission system as claimed in claim 10, wherein said pulse generating means is further characterized as capable of producing initially a positive pressure phase.

13. An ultrasonic transmission system for the treatment of pathological tissue by producing controlled cavitation in the pathological tissue comprising:
    an ultrasonic pulse generating means comprising:
    means for generating an ultrasonic signal having a carrier frequency exceeding 20 kHz;
    means for generating pulses for controlled pathological tissue cavitation, said pulse generating means coupled to said signal generating means to generate briefly emitted pulses of said ultrasonic signal, each pulse having at least one rarfaction phase of negative sonic pressure amplitude exceeding $2 \times 10^5$ Pa in value, a pulse duration (T) of less than 100 $\mu$s, and a pulse recurrence rate of less than 1/(5T); and
    means for focussing said ultrasonic pulses, said focussing means positioned with respect to said ultrasonic pulse generating means to focus the ultrasonic pulses generated therefrom upon a focal point whereby location of pathological tissue at the focal point of said focussing means and generation of ultrasonic pulses by way of a coupling medium by said ultrasonic pulse generating means upon the pathological tissue so located effects the destruction thereof by controlled cavitation,
    said pulse generating means producing at said focal point a pulse envelope amplitude profile which is adapted to the treatment that is needed, and
    said focussing means further comprising two mutually confronting focussing reflectors, one of which reflects in a soft manner and the other of which reflects in a hard manner, said reflectors spatially positioned and offset with respect to said ultrasonic signal producing means and said pulse generating means so that said signal is a signal of alternative prefix and is produced in the common focal area of said reflectors.

14. The ultrasonic transmission system as claimed in claim 13, wherein said pulse generating means is further characterized as capable of producing initially a rarefaction phase.

15. The ultrasonic transmission system as claimed in claim 13, wherein said pulse generating means is further characterized as capable of producing initially a positive pressure phase.

16. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 $\mu$s, and a pulse recurrence rate less than 1/(5T), and each pulse having at said focus a pulse envelope amplitude profile which is adapted to the treatment that is needed, said profile having the shape of an exponential function.

17. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 $\mu$s, and a pulse recurrence rate less than 1/(5T), and each pulse having at said focus a pulse envelope amplitude profile which is adapted to the treatment that is needed, said profile having the shape of a Gaussian function.

18. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 $\mu$s, and a pulse recurrence rate less than 1/(5T), and each pulse having at said focus a pulse envelope amplitude profile which is adapted to the treatment that is needed, said profile being a stepped profile.

19. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 $\mu$s, and a pulse recurrence rate less than 1/(5T), and each pulse having at said focus a pulse envelope amplitude profile which is adapted to the treatment that is needed, said profile having the shape of a sloping linear function.

20. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 $\mu$s, and a pulse recurrence rate less than 1/(5T), and each pulse having at said focus a pulse envelope amplitude profile which is adapted to the treatment that is needed, said profile being a rectangular envelope profile.

21. The method of claim 20, wherein a pulse begins with said rarefaction phase.

22. The method of claim 21, wherein the carrier frequency lies between 0.2 and 4 MHz, the duration of each said rarefaction phase being less than 2.5 $\mu$s.

23. The method of claim 20, wherein the duration of pulse measured at said focus is equal to the period of the carrier frequency and the beginning of the pulse is synchronized with the passage through zero of the carrier frequency.

24. The method of claim 20, wherein the carrier frequency lies between 0.2 and 4 MHz, the duration of each said rarefaction phase being less than 2.5 $\mu$s.

25. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 $\mu$s, and a pulse recurrence rate less than 1/(5T), and each pulse having at said focus a pulse envelope amplitude profile which is adapted to the treatment that is needed;
said step is emitting an ultrasonic signal comprising the step of generating said signal using the steam bubble explosion principle; and
said step of producing controlled cavitation comprising the steps of reflecting the signal both off a first focussing reflector in a soft manner and off a second focussing reflector in a hard manner, said reflections occurring so as to produce a signal of alternative prefix and to produce controlled cavitation in a common focal area of the first reflector and of a twin reflector formed by the combination of the first and second reflectors.

26. The method of claim 25, wherein a pulse begins with said rarefaction phase.

27. The method of claim 25, wherein a pulse begins with a positive pressure phase.

28. A method of treating pathological tissue using an ultrasonic signal comprising the steps of:
providing an ultrasonic transmission system capable of producing an ultrasonic signal at a focus of the system;
locating tissue to be treated;
producing controlled cavitation in the tissue to be treated by operating the system to emit an ultrasonic signal formed of pulses focussed on the tissue to be treated, each pulse having at least one rarefaction phase of negative sonic pressure amplitude exceeding $2 \times 10^5$ Pa, the signal having a carrier frequency greater than 20 kHz, a pulse duration (T) less than 100 μs, and a pulse recurrence rate less than 1/(5T), and each pulse having at said focus a pulse envelope amplitude profile which is adapted to the treatment that is needed;
said step of emitting an ultrasonic signal comprising the step of generating said signal using the steam bubble explosion principle; and
said step of producing controlled cavitation comprising the steps of reflecting the signal both off first and second mutually confronting focussing reflectors, reflection off the first focussing reflector occurring in a soft manner, reflection off the second focussing reflector occurring in a hard manner, said reflections occurring so as to produce a signal of alternative prefix and to produce controlled cavitation in a common focal area of said reflectors.

29. The method of claim 28, wherein a pulse begins with said rarefaction phase.

30. The method of claim 28, wherein a pulse begins with a positive pressure phase.

* * * * *